(12) United States Patent
Corbett

(10) Patent No.: US 9,278,189 B2
(45) Date of Patent: Mar. 8, 2016

(54) APPARATUS FOR SIMULTANEOUSLY DELIVERING FLUID TO A DUAL LUMEN CATHETER WITH A SINGLE FLUID SOURCE

(75) Inventor: Scott C. Corbett, Beverly, MA (US)

(73) Assignee: ABIOMED, INC., Danvers, MA (US)

(*) Notice: Subject to any disclaimer, the term of this patent is extended or adjusted under 35 U.S.C. 154(b) by 771 days.

(21) Appl. No.: 13/395,005

(22) PCT Filed: Sep. 9, 2010

(86) PCT No.: PCT/US2010/048278
§ 371 (c)(1),
(2), (4) Date: Oct. 25, 2012

(87) PCT Pub. No.: WO2011/031864
PCT Pub. Date: Mar. 17, 2011

(65) Prior Publication Data
US 2013/0053622 A1  Feb. 28, 2013

Related U.S. Application Data

(60) Provisional application No. 61/240,887, filed on Sep. 9, 2009.

(51) Int. Cl.
*A61M 1/10* (2006.01)
*A61M 25/00* (2006.01)
(Continued)

(52) U.S. Cl.
CPC ........... *A61M 25/0014* (2013.01); *A61M 1/102* (2014.02); *A61M 1/1008* (2014.02);
(Continued)

(58) Field of Classification Search
CPC .............. A61M 1/1008; A61M 1/102; A61M 2039/1083; A61M 2039/1088; A61M 25/0021; A61M 25/0068; A61M 2025/0031; A61M 2025/0037; A61B 5/021–5/0235
USPC ........................................ 600/16–18; 604/284
See application file for complete search history.

(56) References Cited

U.S. PATENT DOCUMENTS 5,423,323 A * 6/1995 Orth ............................. 600/486
5,827,223 A * 10/1998 Butterfield ...................... 604/65
(Continued)

FOREIGN PATENT DOCUMENTS

| JP | 2004-230032 | 8/2004 |
|----|-------------|--------|
| JP | 2008-178690 | 8/2008 |

OTHER PUBLICATIONS

International Preliminary Report on Patentability for PCT/US2010/048278 dated Mar. 22, 2012.
(Continued)

*Primary Examiner* — Eugene Wu
(74) *Attorney, Agent, or Firm* — Ropes & Gray LLP

(57) ABSTRACT

An apparatus comprising an input connector configured for sterile connection to a fluid source, a first tube, a second, and a third tube. The first tube extends from a proximal end to a distal end, the proximal end comprising an input connector configured for sterile attachment to a fluid source. The input connector provides fluid communication between the first tube and the source. The second and third tubes are each in fluid communication with the first tube. The second and third tubes each extend from a proximal end to a distal end comprising an output connector configured for sterile connection to separate fluid input ports of a catheter based device.

8 Claims, 4 Drawing Sheets

(51) Int. Cl.
*A61M 5/162* (2006.01)
*A61M 5/148* (2006.01)
*A61M 39/00* (2006.01)

(52) U.S. Cl.
CPC ............ *A61M 5/162* (2013.01); *A61M 5/1486* (2013.01); *A61M 2039/0018* (2013.01); *A61M 2205/6081* (2013.01)

(56) References Cited

U.S. PATENT DOCUMENTS 5,911,685 A * 6/1999 Siess et al. ...................... 600/16
5,921,965 A    7/1999 Blei
5,964,694 A * 10/1999 Siess et al. ...................... 600/17
2004/0236286 A1   11/2004 Klein
2006/0161095 A1*  7/2006 Aboul-Hosn et al. ............ 604/9

OTHER PUBLICATIONS

International Search Report for PCT/US2010/048278 dated Nov. 25, 2010.
Office Action for Australian Appl. Ser. No. 2010292247 dated Jan. 14, 2014.
Office Action for EPO Appl. Ser. No. 10754390.2 dated Apr. 18, 2012.
Office Action for EPO Appl. Ser. No. 10754390.2 dated Jun. 24, 2013.
Office Action for Japanese Appl. Ser. No. 2012-528896 dated Jun. 4, 2014.

* cited by examiner

APPARATUS FOR SIMULTANEOUSLY DELIVERING FLUID TO A DUAL LUMEN CATHETER WITH A SINGLE FLUID SOURCE

CROSS-REFERENCE TO RELATED PATENT APPLICATIONS

This application is a U.S. National Stage of PCT International Application Number PCT/US2010/048278, filed Sep. 9, 2010, which claims benefit of U.S. Provisional Application Ser. No. 61/240,887, filed Sep. 9, 2009. The entire contents of the foregoing applications are hereby incorporated herein by reference.

BACKGROUND

The present disclosure relates generally to the field of medical devices. More specifically, the present disclosure relates to fluid delivery systems for medical devices.

An intracardiac blood pump is a blood pump that is at least partially introduced into the heart to deliver blood from the heart into an artery, wherein the pump may protrude through a surgical opening in the heart. A special form of intracardiac blood pumps are intravascular blood pumps. Intravascular blood pumps are introduced into the heart through the vascular system of the patient, the insertion site being spaced from the heart, such as insertion at the thigh of the patient for access to the femoral artery.

For example, currently known blood pump catheters, such as the Impella 2.5 catheter marketed by Abiomed, include a drive portion including a motor and a pump portion including an impeller driven by the motor, at least one lateral discharge port being provided between the drive portion and the pump portion. Fluids from outside the patient may be delivered through lumens to the drive portion for various purposes. For example, fluids may be delivered the placement signal lumen to facilitate the proper positioning of the drive portion. Fluids may also be delivered to the motor to keep it purged of blood.

As shown in FIG. 1, with currently known blood pump catheters 10, a first fluid, such as a saline solution, may be delivered through the placement signal lumen and a second fluid, such as a glucose solution, may be delivered through the purge lumen. This arrangement requires two fluid sources 12 and 14 and requires that two sets of tubing 16 and 18 pass into the sterile field and results in excessive clutter. Further, a device such as an auxiliary pump 19 may be required to deliver the second fluid from the second fluid source 14 to the purge lumen. The auxiliary pump 19 can be difficult to use to those unfamiliar with it. Further, the auxiliary pump is another device that must be in close proximity to the sterile field, causing additional clutter.

Devices such as the blood pump catheter device 10 may need to be deployed quickly in emergency scenarios. It would be advantageous to provide an improved apparatus for delivering fluids for multiple uses to a catheter with multiple lumens to reduce the set-up time needed for such a device.

It would be advantageous to provide a fluid delivery apparatus with reduced clutter in the area of the sterile field.

It would be advantageous to provide a method for using a fluid delivery apparatus with a familiar, easy to use interface for medical practitioners performing or assisting with a medical procedure including a multiple lumen catheter.

SUMMARY

One embodiment relates to an apparatus comprising an input connector configured for sterile connection to a fluid source, a first tube, a second tube, and a third tube. The first tube extends from a proximal end to a distal end, the proximal end comprising an input connector configured for sterile attachment to a fluid source. The input connector provides fluid communication between the first tube and the source. The second tube and the third tube are each in fluid communication with the first tube. The second tube and the third tube each extend from a proximal end to a distal end comprising an output connector configured for sterile connection to a fluid input port of a catheter based device.

Another embodiment relates to a method of operating a catheter based device having at least two fluid inputs ports. The method includes providing a fluid delivery apparatus comprising a first tube, a second tube, and a third tube. The first tube extends from a proximal end to a distal end, the proximal end comprising an input connector configured for sterile attachment to a fluid source to provide fluid communication between to first tube and the source. The second tube and the third tube are each in fluid communication with the first tube. The second tube and the third tube each extend from a proximal end to distal end comprising an output connector configured for sterile connection to a fluid input port of a catheter based device. The method further includes connecting the input connector of the first tube to the fluid source; connecting the output connector of the second tube to a first fluid input port of the catheter based device; and connecting the output connector of the third tube to a second fluid input port of the catheter based device.

In one aspect, an apparatus is disclosed including: an input connector configured for sterile connection to a fluid source; a first tube extending from a proximal end to a distal end, the proximal end including an input connector configured for sterile attachment to a fluid source to provide fluid communication between the first tube and the source; and a second and a third tube, each in fluid communication with the first tube and each extending from a proximal end to a distal end including an output connector configured for sterile connection to a fluid input port of a catheter based device.

In some embodiments, fluid input into proximal end of the first tube from the fluid source will flow through the first tube to the distal end and be divided into at least: a) a first portion flowing through the second tube from the proximal end of the second tube to distal end of the second tube, and b) a second portion flowing through the third tube from the proximal end of the third tube to distal end of the third tube.

In some embodiments, the at least one of the input connector and the output connecters is a Luer connector.

In some embodiments, each of the output connectors is a male Luer connector.

Some embodiments include the fluid source, and where the fluid source includes a pressure bag.

Some embodiments include the catheter based device. In some embodiments, the catheter based device is a percutaneous ventricle assist device having a first fluid input port for a pump purge line and a second fluid input port for a placement signal line. In some embodiments, the output connector of the second tube provides fluid communication between the second tube and the first fluid input port. In some embodiments, the output connector of the third tube provides fluid communication between the third tube and the second fluid input port.

In another aspect, a method is disclosed of operating a catheter based device having at least two fluid inputs ports including: providing a fluid delivery apparatus including: an input connector configured for sterile connection to a fluid source; a first tube extending from a proximal end to a distal end, the proximal end including an input connector configured for sterile attachment to a fluid source to provide fluid communication between the first tube and the source; and a second and a third tube, each in fluid communication with the first tube and each extending from a proximal end to distal end including an output connector configured for sterile connection to a fluid input port of a catheter based device. The method includes connecting the input connector of the first tube to the fluid source; connecting the output connector of the second tube to a first fluid input port of the catheter based device; and connecting the output connector of the third tube to a second fluid input port of the catheter based device.

Some embodiments include inputting fluid into proximal end of the first tube from the fluid source, thereby causing flow through the first tube to the proximal end and be divided into at least: a) a first portion flowing through the second tube from the proximal end of the second tube to distal end of the second tube, and b) a second portion flowing through the third tube from the proximal end of the third tube to distal end of the third tube.

In some embodiments, the fluid source is a pressure bag, and where the inputting fluid includes applying pressure to the pressure bag.

In some embodiments, the applying pressure to the pressure bag includes maintaining at least a minimum pressure on fluid in the pressure bag to provide an uninterrupted flow of fluid from the bag to each of the first and second fluid input ports.

In some embodiments, the catheter based device is a percutaneous ventricular assist device; the first fluid input port is a port for a pump purge line of the percutaneous ventricular assist device; and the second fluid input port is a port for a placement signal line percutaneous ventricular assist device.

Some embodiments include: causing fluid from the fluid source to flow from the second tube into the first fluid input port and through the pump purge line to a pump of the percutaneous ventricle assist device located in a blood vessel of a patient to maintain the pump substantially free of blood.

Some embodiments include: causing fluid from the fluid source to flow from the third tube into the second fluid input port to a placement signal line; and using fluid in the placement signal line to measure a pressure signal indicative of the placement of the percutaneous ventricular assist device in a cardiac structure, or blood vessel of a patient.

In some embodiments, the pressure signal is indicative of the ventricular, or arterial pulse of the patient.

In some embodiments, connecting the input connector of the first tube to the fluid source includes forming a sterile fluid connection between the first tube and the fluid source; connecting the output connector of the second tube to a first fluid input port of the catheter based device includes forming a sterile fluid connection between the second tube and the first fluid input port; and connecting the output connector of the third tube to a second fluid input port of the catheter based device includes forming a sterile fluid connection between the third tube and the second fluid input port.

In some embodiments, the at least one of the input connector and the output connecters is a Luer connector.

In some embodiments, each of the output connectors is a male Luer connector.

Various embodiments may include any of the above features, elements, techniques, etc., either alone or in any suitable combination.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION

Figure 2:
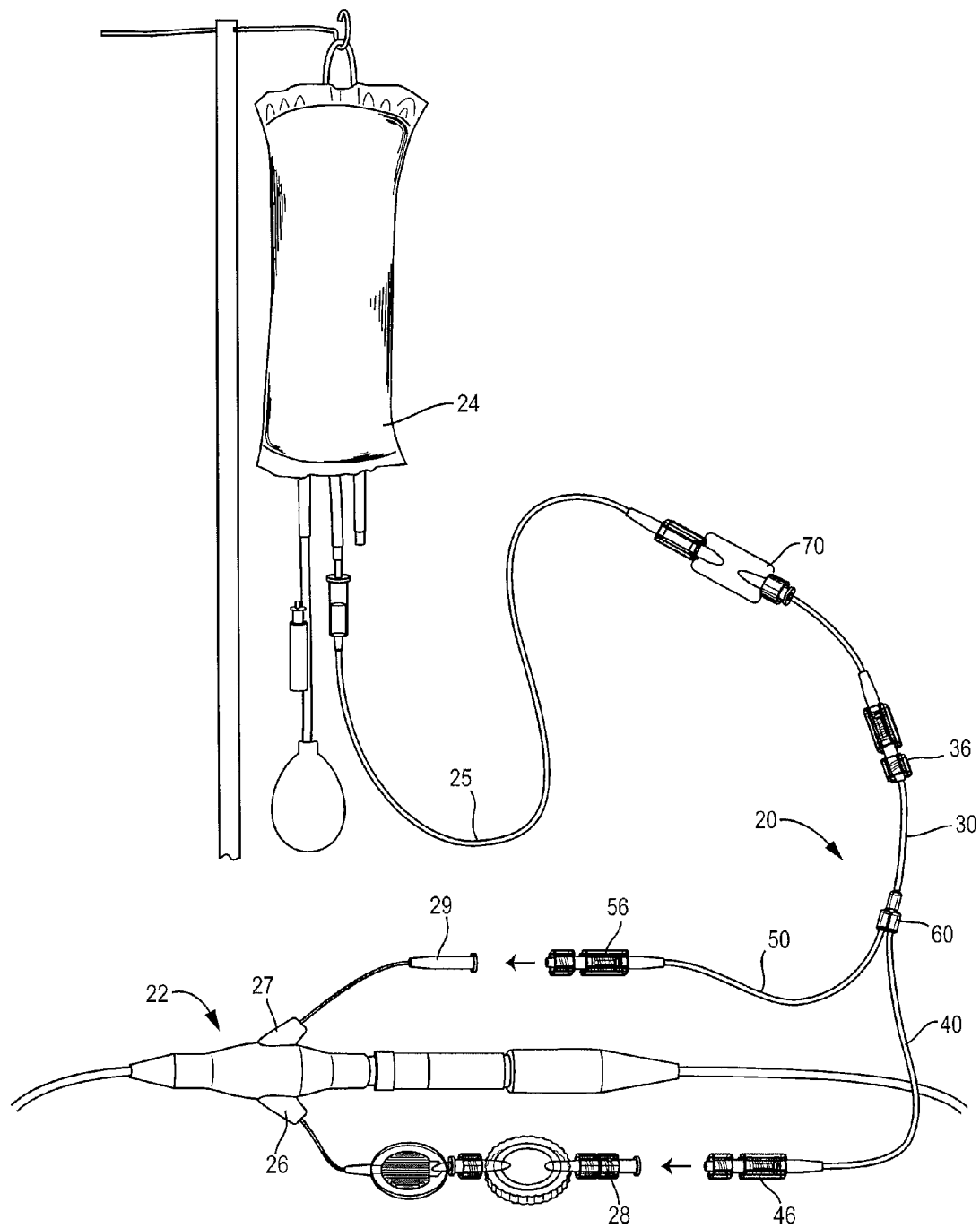
FIG. 2 is a schematic view of an improved fluid delivery apparatus for a dual lumen catheter according to an exemplary embodiment.
Figure 3:
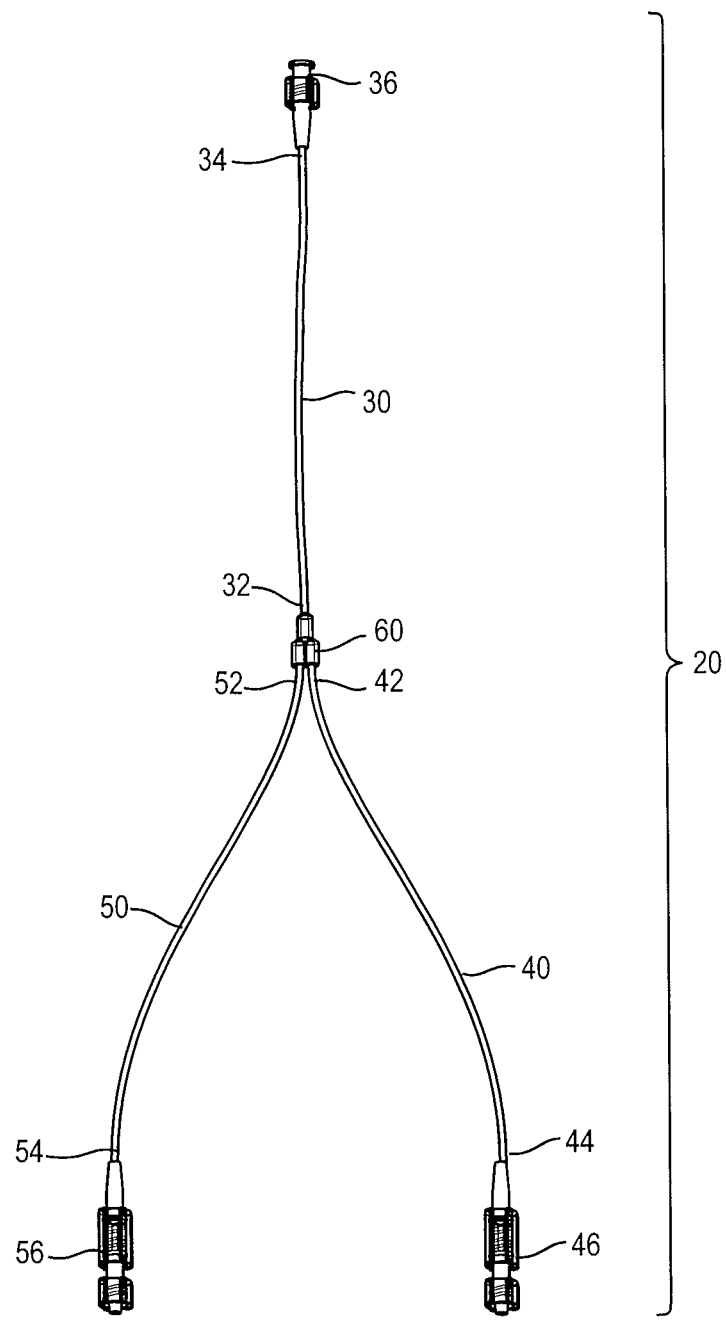
FIG. 3 is a detailed schematic view of a portion of the fluid delivery apparatus for a dual lumen catheter of FIG. 2.

Referring to FIGS. 2-3, a fluid delivery apparatus 20 is shown according to an exemplary embodiment, coupling a medical device (shown as a multiple-lumen catheter device 22) to a fluid source 24. The fluid delivery apparatus 20 is configured to allow medical personnel to quickly and efficiently connect the device 22 to a fluid source 24 with reduced clutter in the area of the sterile field.

The fluid delivery apparatus 20 includes a first tube 30 (e.g., input tube), a second tube 40 (e.g., first output tube), and a third tube 50 (e.g., second output tube) coupled together by a y-shaped connector 60. The fluid delivery apparatus 20 is configured to allow fluid from a single fluid source 24 to be delivered to two inputs 26 and 27 of the medical device 22. According to an exemplary embodiment, the first fluid input port 26 and the second fluid input port 27 are coupled to two lumens for the device 22.

Referring to FIG. 3, the first tube 30 extends from a distal end 32 coupled to the y-shaped connector 60 to a proximal end 34 coupled to an input connector 36 (e.g., fitting, coupling, etc.). The input connector 36 is coupled to a connector for a tube 25 extending from the fluid source 24. The input connector 36 may be connected directly to the tube 25 extending from the fluid source 24 or may be connected via another device, as shown in FIG. 2. The input connector 36 is configured to provide a sterile attachment to the fluid source 24 to provide fluid communication between the fluid source 24 and the first tube 30. The input connector 36 may be, for example, a female Luer connector that is permanently coupled to the proximal end 34 of the first tube 30 (e.g., fused via heat, solvents or adhesive) and configured to be coupled to a corresponding male Luer connector. In other embodiments, the input connector 36 may be removably coupled to the proximal end 34 of the first tube 30 (e.g., via a screw-type or pressure fitting, etc.). In some embodiments, the female Luer connector 20 at the end of the first tube 30 may either be bonded or removably coupled to an end of the tube 25 extending from the fluid source 24, e.g., via a male Luer connector located at the end of the tube 25.

According to an exemplary embodiment, the fluid source 24 may be a commonly used device such as a pressure bag containing a useful fluid such as a saline solution (NaCL), a glucose solution, or any other fluid that may be supplied to the medical device 22. The fluid may be chosen to be compatible with the medical device 22. For example, in embodiments where the medical device 22 includes a metallic pump motor, use of saline solution or other potentially corrosive fluids should be avoided. Connections to a commonly used fluid source 24 such as a pressure bag via a commonly used input connector 36 such as a Luer connector is familiar to medical personnel and allows for quick connection of the fluid delivery apparatus 20 to the fluid source 24.

An in-line pressure transducer 70 may be coupled to the first tube 25. The pressure transducer 70 measures the pressure of fluid in the fluid delivery apparatus 20. The pressure transducer 70 may be coupled to a console or other device to display the fluid pressure to medical personnel.

Referring still to FIG. 3, the y-shaped connector 60 divides the incoming fluid stream through the first tube 30 into two outgoing fluid streams through the second tube 40 and the third tube 50. The second tube 40 extends from a proximal end 42 coupled to the y-shaped connector 60 to a distal end 44 coupled to an output connector 46 (e.g., fitting, coupling, etc.). The third tube 50 likewise extends from a proximal end 52 coupled to the y-shaped connector 60 to a distal end 54 coupled to an output connector 56 (e.g., fitting, coupling, etc.). The output connectors 46 and 56 are coupled to connectors 28 and 29 of the device 22, respectively. The output connectors 46 and 56 are configured to provide a sterile attachment to the fluid input ports 26 and 27 of the device 22 via connectors 28 and 29. The output connector 46 of the second tube 40 provides fluid communication between the second tube 40 and the first fluid input port 26. The output connector 56 of the third tube 50 provides fluid communication between the third tube 50 and the second fluid input port 27. Note that, in some embodiments, the y-shaped connector 60, may be formed integrally with the first, second and third tubes, e.g., such that the first tube 30 bifurcates to form the second and third tubes 40, and 50.

In various embodiments, the first, second, and third tubes 30, 40, and 50 may be of any suitable length. For example, in some embodiments, the second and third tubes 40, and 50 may be of differing length to facilitate easy connection and fit to the medical device 22.

Similar to the input connector 36, the output connectors 46 and 56 may be, for example, male Luer connectors that are permanently coupled to the distal end 44 of the second tube 40 and the distal end 54 of the third tube 50 (e.g., fused via heat, solvents or adhesive) and configured to be coupled to a corresponding female Luer connectors. In other embodiments, the output connectors 46 and 56 may be removably coupled to the distal end 44 of the second tube 40 and the distal end 54 of the third tube 50 (e.g., via a screw-type or pressure fitting, etc.).

The output connectors 46 and 56 may be color coded to the connectors 28 and 29 for the fluid input ports 26 and 27 of the device 22. Color coding provides an easy method to use visual indication of how the fluid delivery apparatus 20 should be properly coupled to the device 22. The device 22 may also include other visual indications, such as symbols or tags instead of or in addition to color coding to further facilitate the proper coupling of the fluid delivery apparatus 20 to the device 22.

According to an exemplary embodiment, the device 22 is a percutaneous ventricle assist device catheter based device with multiple lumens. The first fluid input port 26 is connected to a first lumen providing a pump purge line. The fluid provided to the first fluid input port 26 via the second tube 40 flushes the pump motor of the ventricular assist device to keep it clear of blood. The fluid provided to the first input port 26 via the second tube 40 provides a pressure reading to the pressure transducer 70. The second fluid input port 27 is connected to a second lumen providing a placement signal line. The fluid provided to the second input port 27 via the third tube 50 provides a pressure reading from an additional pressure transducer located in the device 22 (or other suitable location). The reading from the pressure transducer is used to properly locate the ventricular assist device.

In other exemplary embodiments, the device may be any medical instrument that includes multiple functions or subcomponents requiring a sterile fluid.

Figure 4:
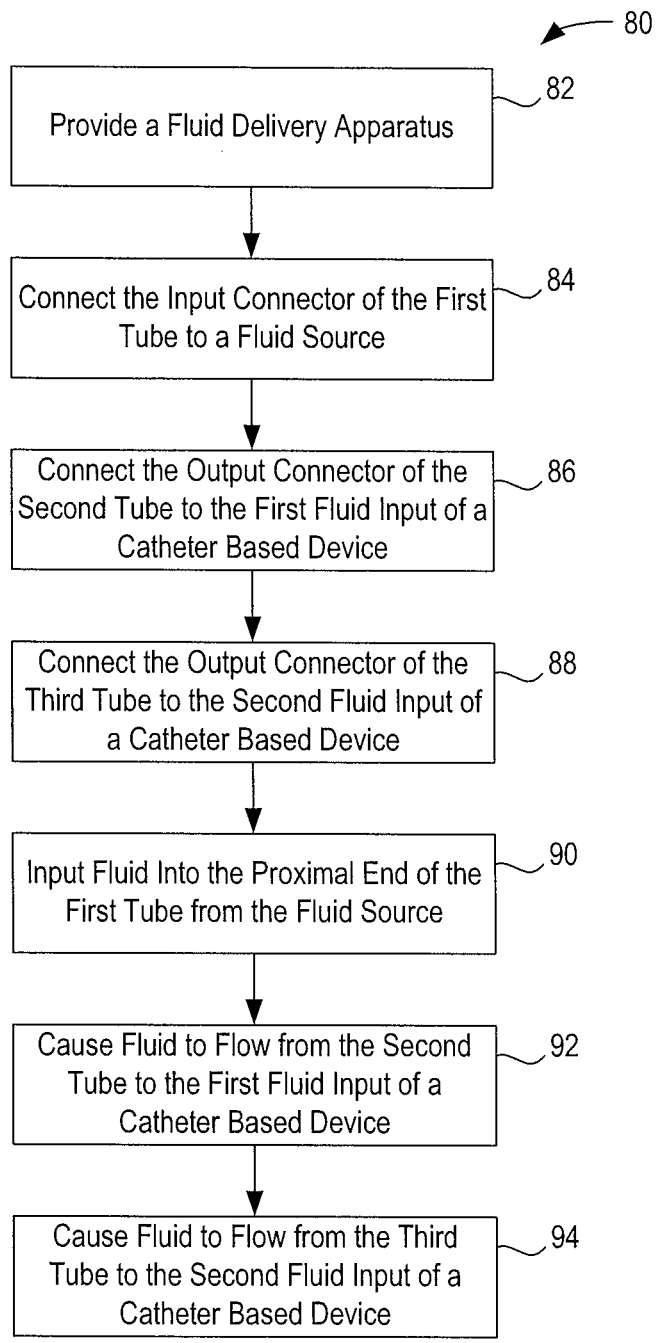
FIG. 4 is a flow diagram of a method of operating a catheter based device having at least two fluid inputs ports is shown according to an exemplary embodiment.

Referring now to FIG. 4, a method 80 of operating a catheter based device having at least two fluid inputs ports is shown according to an exemplary embodiment. A fluid delivery apparatus described above is provided (step 82). The apparatus comprises an input connector configured for sterile connection to a fluid source, a first tube, a second tube, and a third tube. The first tube extends from a proximal end to a distal end, the proximal end comprising an input connector configured for sterile attachment to a fluid source. The input connector provides fluid communication between the first tube and the source. The second tube and the third tube are each in fluid communication with the first tube. The second tube and the third tube each extend from a proximal end to a distal end comprising an output connector configured for sterile connection to a fluid input port of a catheter based device.

The input connector of the first tube is connected to the fluid source (step 84). The output connector of the second tube is connected to a first fluid input port of the catheter based device (step 86). The output connector of the third tube is connected to a second fluid input port of the catheter based device (step 88).

Connecting the input connector of the first tube to the fluid source forms a sterile fluid connection between the first tube and the fluid source. Connecting the output connector of the second tube to a first fluid input port of the catheter based device forms a sterile fluid connection between the second tube and the first fluid input port. Connecting the output connector of the third tube to a second fluid input port of the catheter based device forms a sterile fluid connection between the third tube and the second fluid input port. According to an exemplary embodiment, the input connector and/or the output connectors may be a Luer connector.

After the apparatus is coupled to the fluid source and the fluid input ports of the catheter based device, fluid is input into the proximal end of the first tube from the fluid source (step 90). Optionally, fluid may be applied first to flush the lines 30, 40, and 50, then connections are made to the device 20. Flow is thereby caused through the first tube to the distal end and be divided into at least a first portion flowing through the second tube and a second portion flowing through the third tube. According to an exemplary embodiment, the fluid source is a pressure bag, and applying pressure to the pressure bag inputs fluid into the proximal end of the first tube. A minimum pressure is maintained on the fluid in the pressure bag to provide an uninterrupted flow of fluid from the bag to each of the first and second fluid input ports.

Fluid from the fluid source is caused to flow from the second tube into the first fluid input port and through the pump purge line to a pump of the percutaneous ventricular assist device located in a cardiac structure, or blood vessel of a patient to maintain the pump substantially free of blood (step 92). Fluid from the fluid source is caused to flow from the third tube into the second fluid input port to a placement signal line; and is used in the placement signal line to measure a pressure signal indicative of the placement of the percutaneous ventricle assist device in a cardiac structure, or blood vessel of a patient (step 94). According to an exemplary embodiment, a proper placement of the percutaneous ventricular assist device is indicated by the arterial pulse of the patient.

Figure 1:
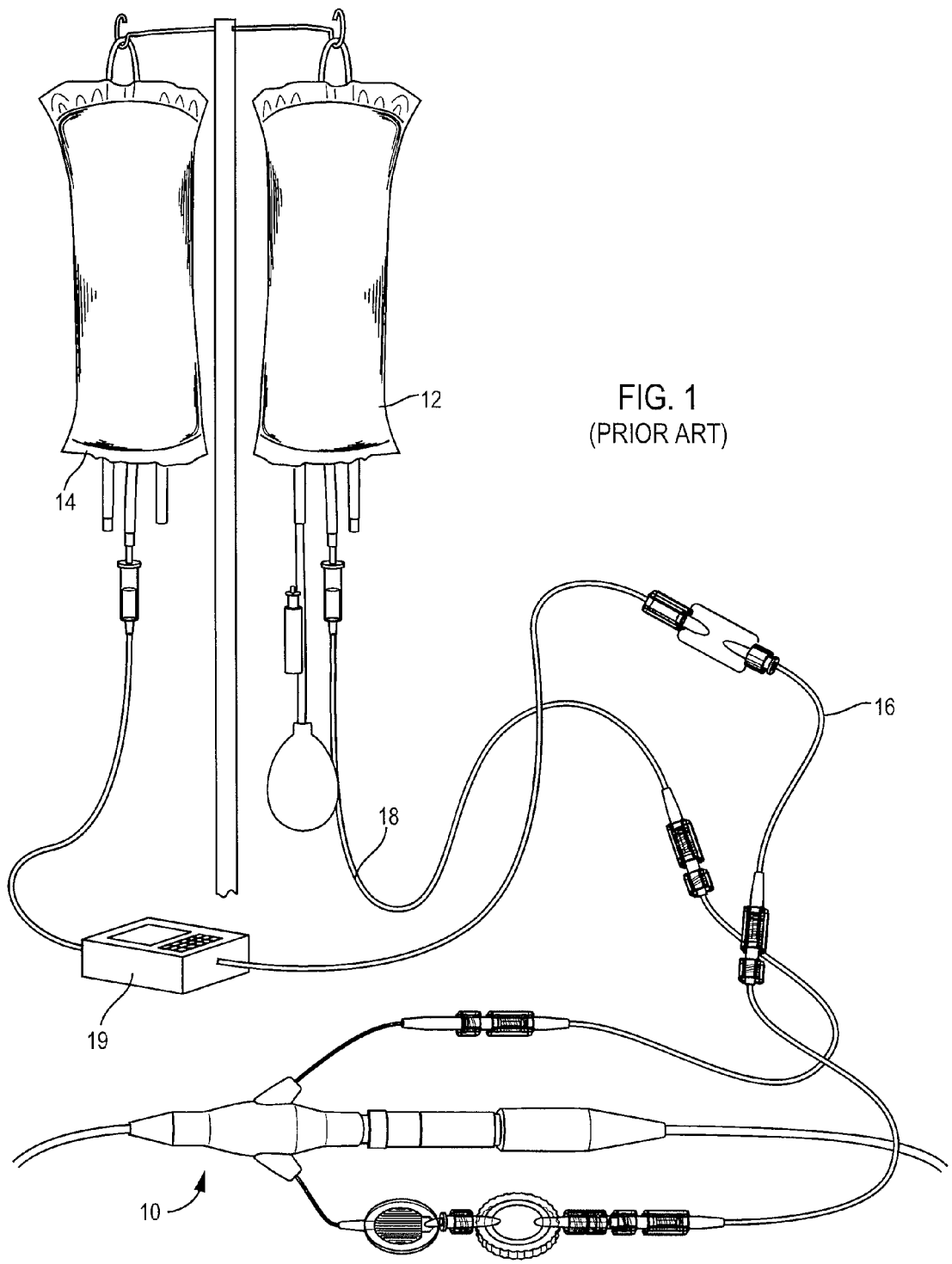
FIG. 1 is a schematic view of a prior art fluid delivery apparatus for a dual lumen catheter.

In some embodiments, the second tube 40, extending to the placement signal line of the medical device 22 may include a clamp (not shown), which can be used to arrest flow through the tube. In some embodiments, this clamp can be closed after placement of the percutaneous ventricle assist device. After clamping, pressure bag fluid source 24 may be replaced with an infusion pump, to allow operation similar to that shown FIG. 1.

The construction and arrangement of the elements of the fluid delivery apparatus and method as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, setup sequence, use of materials, colors, orientations, etc.) without materially departing from the novel teachings and advantages of the subject matter recited herein. For example, elements shown as integrally formed may be constructed of multiple parts or elements, the position of elements may be reversed or otherwise varied, and the nature or number of discrete elements or positions may be altered or varied. It should be noted that the elements and/or assemblies of the system may be constructed from any of a wide variety of materials that provide sufficient strength, durability, or biocompatibility. Other substitutions, modifications, changes and omissions may be made in the design, operating conditions and arrangement of the preferred and other exemplary embodiments and medical procedures without departing from the scope of the present invention. For example, although a y-shaped device for use with a two-port medical device is shown in the example above, other shapes having three or more output tubes may be used to accommodate three or more ports.

What is claimed is:

1. An apparatus comprising:
a catheter based device;
a first tube extending from a proximal end to a distal end, said proximal end comprising an input connector configured for sterile attachment to a fluid source to provide fluid communication between the first tube and the source; and
a second and a third tube, each in fluid communication with the first tube and each extending from a proximal end to a distal end comprising an output connector configured for sterile connection to a respective fluid input port of the catheter based device;
wherein the catheter based device is a percutaneous ventricle assist device having a first fluid input port for a pump purge line and a second fluid input port for a placement signal line;
wherein the output connector of the second tube provides fluid communication between the second tube and the first fluid input port; and
wherein the output connector of the third tube provides fluid communication between the third tube and the second fluid input port.

2. The apparatus of claim 1, further comprising a visual indication that facilitates proper coupling of the output connectors to the percutaneous ventricle assist device.

3. The apparatus of claim 1, wherein the output connectors are color coded to a respective one of the first and second fluid input ports.

4. The apparatus of claim 1, further comprising a pressure transducer coupled to the first tube.

5. The apparatus of claim 1, wherein fluid input into the proximal end of the first tube from the fluid source will flow through the first tube to the distal end of the first tube and be divided into at least:
   a) a first portion flowing through the second tube from the proximal end of the second tube to distal end of the second tube, and
   b) a second portion flowing through the third tube from the proximal end of the third tube to distal end of the third tube.

6. The apparatus of claim 5, wherein the at least one of the input connector and the output connecters is a Luer connector.

7. The apparatus of claim 6, wherein each of the output connectors is a male Luer connector.

8. The apparatus of claim 1, further comprising the fluid source, and wherein the fluid source comprises a pressure bag.

* * * * *